United States Patent [19]

Fankhauser et al.

[11] Patent Number: 5,538,944
[45] Date of Patent: Jul. 23, 1996

[54] COMPOSITION CONTAINING A PREPONDERANT AMOUNT OF (1RS,5RS)-5-METHYL-EXO-TRICYCLO [6.2.1.0²,⁷]UNDECAN-4-ONE AND ITS USE IN PERFUMERY

[75] Inventors: Peter Fankhauser, Meyrin; Piero Fantini, Geneva; Pierre-Alain Blanc, Crassier, all of Switzerland

[73] Assignee: Firmenich S.A., Geneva, Switzerland

[21] Appl. No.: 404,407

[22] Filed: Mar. 14, 1995

[30] Foreign Application Priority Data

Apr. 22, 1994 [CH] Switzerland .............................. 1255/94

[51] Int. Cl.⁶ ....................................................... A61K 7/46
[52] U.S. Cl. ................................................ 512/15; 568/373
[58] Field of Search ................................ 512/15; 568/373

[56] References Cited

U.S. PATENT DOCUMENTS 3,968,070  7/1976  Sundt ...................................... 260/348

FOREIGN PATENT DOCUMENTS 74 24334  7/1974  France ..................................... 512/15

*Primary Examiner*—James H. Reamer
*Attorney, Agent, or Firm*—Pennie & Edmonds

[57] ABSTRACT

(1RS,5RS)-5-Methyl-exo-tricyclo[6.2.1.0$^{2,7}$]undecan-4-one, as well as the compositions which contain a preponderant amount of this compound together with its isomer (1RS, 5SR)-5-methyl-exo-tricyclo[6.2.1.0$^{2,7}$]undecan-4-one, are useful as perfuming ingredients for the preparation of perfuming compositions and perfumed articles, to which they impart aromatic, thujonic and herbaceous odors.

13 Claims, No Drawings

COMPOSITION CONTAINING A PREPONDERANT AMOUNT OF (1RS,5RS)-5-METHYL-EXO-TRICYCLO [6.2.1.0²,⁷]UNDECAN-4-ONE AND ITS USE IN PERFUMERY

BRIEF SUMMARY OF THE INVENTION

The invention relates to a composition of matter consisting of a mixture which contains a preponderant amount of (1RS,5RS)-5-methyl-exo-tricyclo[6.2.1.0$^{2,7}$]undecan-4-one, together with a lesser amount of (1RS,5SR)- 5-methyl-exo-tricyclo[6.2.1.0$^{2,7}$]undecan-4-one.

The invention further concerns a composition of matter consisting of essentially pure (1RS,5RS)-5-methyl-exo-tricyclo[6.2.1.0$^{2,7}$]undecan-4-one.

Another object of the invention is a method to impart, improve, enhance or modify the odor properties of a perfuming composition or of a perfumed article, which consists in adding to said composition or article a fragrance effective amount of the composition of matter above-cited.

The invention further relates to the perfuming compositions and perfumed articles obtained by this method.

The invention also provides a process for the preparation of the above-cited composition of matter, which process comprises treating a mixture of (1RS,5RS)-5-methyl-exo-tricyclo[6.2.1.0$^{2,7}$]undecan-4-one and (1RS,5SR)-5-methyl-exo-tricyclo[6.2.1.0$^{2,7}$]undecan-4-one, wherein the latter is present in a preponderant amount, with a strong organic or inorganic base.

BACKGROUND AND DETAILED DESCRIPTION OF THE INVENTION

The present invention relates to the field of perfumery and concerns more particularly a composition of matter as above-described.

It has been described in the prior art that 5-methyl-tricyclo[6.2.1.0$^{2,7}$]undecan-4-one can be used in perfumery to develop the floral character of the compositions into which it is incorporated, as well as to provide a fixative and reinforcing effect (see, for example, U.S. Pat. No. 3,968,070).

This patent also describes a process for the preparation of 5-methyl-tricyclo[6.2.1.0$^{2,7}$]undecan-4-one, according to the following reaction scheme:

SCHEME I

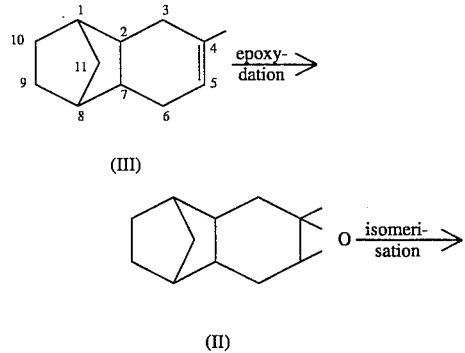

-continued
SCHEME I

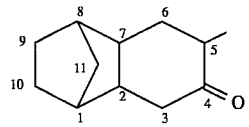

but has strictly no indication regarding the isomeric composition of the product thus obtained. While reproducing the described process, we discovered that the product obtained is in fact a mixture which essentially contains (1RS,5SR)-5-methyl-exo-tricyclo[6.2.1.0$^{2,7}$]undecan-4-one, together with a minor amount, of the order of 20 to 25% by weight, of the corresponding (1RS,5RS) isomer.

Since U.S. Pat. No. 3,968,070 is perfectly silent as regards the isomeric nature of the product obtained, one has to conclude that the authors of the invention there-described totally overlooked the distinctive character of the odor of each individual isomer present in the mixture.

Yet, we have now discovered that (1RS,5RS)-5-methyl-exo-tricyclo[6.2.1.0$^{2,7}$]undecan-4-one, having the formula

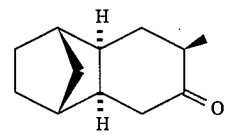

possesses odor properties which are quite distinct from those of its configuration isomer of formula

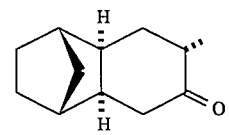

and, furthermore, entirely different from those of the product described in U.S. Pat. No. 3,968,070.

This discovery has been made possible as a result of the process previously cited and described in detail hereinafter, which is also the object of the invention and which makes it possible to obtain compositions of matter enriched in compound (Ia), the properties of which turn out to be clearly superior, from an olfactive point of view, to those of the prior described compositions containing essentially compound (Ib).

It has actually been ascertained that compound (Ia) possesses an aromatic odor with a strong thujonic connotation, a very natural, slightly camphoraceous and herbaceous fragrance, which is reminiscent of the odor of myrtle and cedarleaf. It is moreover a very powerful and tenacious note, both on smelling-strip and on fabrics perfumed by way of this compound.

As for compound (Ib), it has been found to possess a distinctly less aromatic-thujonic odor note, far more camphoraceous, than that of compound (Ia), with a clear fruity connotation, some aspects of which are reminiscent of rhubarb jam or jelly. This is a less powerful odor than that of compound (Ia), and distinctly less elegant in the aromatic thujonic character which is particularly prized by the perfumers.

Even if the above-mentioned odor characters are best represented in the pure or essentially pure compound (Ia), the same sought-after aromatic, thujonic, myrtle and cedar-leaf connotations can be found in the odor of the mixtures of the two isomers (Ia) et (Ib) which contain a preponderant amount, i.e. more than 50% by weight, of the former. These mixtures where compound (Ia) predominates are also an object of the invention and the compositions consisting of at least about 75% by weight of (1RS,5RS)-5-methyl-exo-tricyclo[6.2.1.0$^{2,7}$]undecan-4-one and a definite amount, but not more than about 25% by weight, of (1RS,5SR)-5-methyl-exo-tricyclo[6.2.1.0$^{2,7}$]undecan-4-one are preferred embodiments of the invention. Such compositions can be directly obtained by the process according to the invention and are therefore economically advantageous over the pure compound (Ia), which pure compound requires the further use of preparative chromatography or fractional distillation for its preparation.

When compared with the prior art product described in U.S. Pat. No. 3,968,070, which is essentially composed of (1RS,5SR)-5-methyl-exo-tricyclo[6.2.1.0$^{2,7}$]undecan-4-one, the compositions of the invention provide far more natural and marked aromatic-thujonic effects, as a result of the fact that the camphoraceous connotation of the prior known compound has a tendency to reduce or dampen the freshness of said aromatic notes. The fragrance effect achieved with the prior art mixture is therefore entirely distinct from that imparted by compound (Ia) of the present invention and by the mixtures enriched in this compound, a surprising result in view of the prior art, which is totally silent in this respect, and a result which is clearly apparent from the application examples presented further on.

According to the invention, compound (Ia) and the mixtures rich in this compound, i.e. which contain a predominant amount thereof, can be added to the compositions and articles that one desires to perfume in a wide variety of concentrations. The latter are dependent on the odor effect sought, as well as on the nature of the other ingredients present in a given perfuming composition. By way of example, concentrations of the order of 1 to 10%, or even 20% by weight of the compound or mixture according to the invention, relative to the weight of the perfuming base or concentrate into which they are incorporated, can be cited. Concentration values below those cited will normally be used when perfuming a variety of consumer products such as soaps, bath or shower gels, shampoos or hair-conditioners, cosmetic preparations, body or air deodorants, or yet detergents or fabric softeners and household products.

In such applications, (1RS,5RS)-5-methyl-exo-tricyclo[6.2.1.0$^{2,7}$]undecan-4-one and the compositions of matter according to the invention can be used on their own or in admixture with other perfuming ingredients, solvents or adjuvants of current use in perfumery.

The present invention also relates to a novel process for the preparation of a composition containing a preponderant amount of (1RS,5RS)-5-methyl-exo-tricyclo[6.2.1.0$^{2,7}$]undecan-4-one, which process comprises treating a mixture of (1RS,5RS)-5-methyl-exo-tricyclo[6.2.1.0$^{2,7}$]undecan-4-one and (1RS,5SR)-5-methyl-exo-tricyclo[6.2.1.0$^{2,7}$]undecan-4-one, wherein the latter is present in a preponderant amount, with a strong organic or inorganic base.

As the strong base, there will be preferentially used an alkali metal alkoxide or hydroxide, for example sodium methylate or potassium hydroxide. Other convenient strong bases are the tertiary amines, namely tributylamine.

The reaction can be carried out in an inert organic solvent such as toluene or another hydrocarbon, or yet petroleum ether. Alternatively, it can be carried out without solvent.

The reaction can take place at a wide variety of temperatures, the value of which can be easily optimized as a function of the reaction conditions and so as to guaranty a reaction rate and time adapted to industrial operation.

According to a particular embodiment, the process comprises an optional step according to which the obtained composition is subsequently subjected to preparative chromatography or to fractional distillation, so as to provide essentially pure (1RS,5RS)-5-methyl-exo-tricyclo[6.2.1.0$^{2,7}$]undecan- 4-one, i.e. with a purity above 90%.

The mixture of ketones used as starting product in the process of the invention can be prepared according to reaction scheme I, as is described in U.S. Pat. No. 3,968,070.

According to said U.S. patent, the reaction of epoxidation of 4-methyl-tricyclo[6.2.1.0$^{2,7}$]undec-4-ene can be realized following the usual methods, namely by means of an organic peracid such as for example performic, peracetic, perbenzoic, monoperbenzoic, perphthalic or trifluoroperacetic acid, in the presence of an inert organic solvent such as chloroform, methylene chloride, trichloroethylene, dichloroethane or toluene for example.

In addition, said epoxidation can be carried out in a buffered medium. To this end, one can use an alkaline salt of an organic acid such as for example formic, acetic, propanoic, butyric, oxalic, citric, tartaric or carbonic acid.

The epoxidation reaction can be carried out at a variety of temperatures, the value of which can be optimized as a function of the reaction conditions.

The organic peracids used in said epoxidation can be prepared in situ, by treating an organic add with hydrogen peroxide, in the presence of a mineral acid, following the usual techniques [see for example: H. O. House, Modern Synthetic Reactions, Benjamin, Inc., New York (1965), p. 105 and following].

The exo isomeric configuration of the starting product remains unchanged upon this epoxidation. Moreover, the product of said epoxidation is a mixture of two isomers, represented hereinafter

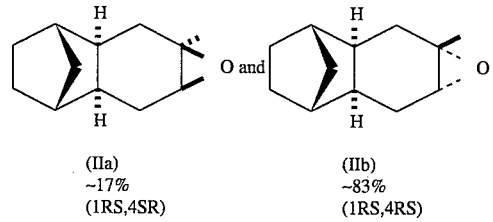

(IIa)  
~17%  
(1RS,4SR)

(IIb)  
~83%  
(1RS,4RS)

The composition of the above-mentioned isomer mixture turns out to be practically independent of the reaction conditions.

The isomerisation of the thus obtained intermediate epoxide is carried out by treating this intermediate compound with an isomerising acidic agent. As acidic agent, there can be used an organic or mineral add, or yet a so-called Lewis acid such as BF$_3$, SnCl$_4$, FeCl$_3$ or AlCl$_3$ for example. The use of BF$_3$ in ether solution is preferred.

Alternatively, the intermediate epoxide can also be converted into the desired ketone via treatment with a heterogeneous acidic catalyst such as an acidic diatomaceous earth, alumina, silica or other.

As previously cited, the product of this epoxidation is a mixture containing a predominant amount of (1RS,5SR)-5-methyl-exo-tricyclo[6.2.1.0$^{2,7}$]undecan-4-one together with minor amounts of its (1RS,5RS) isomer, and it is this mixture that is used as the starting product in the process of the instant invention.

The starting compound (III)—see Scheme I— can be prepared by Diels-Alder cycloaddition between norbornene and isoprene, as is described in U.S. Pat. No. 3,968,070, example 8a. The reaction there-described provides 4-methyl-tricyclo[6.2.1.0$^{2,7}$]undec-4-ene strictly in the exo isomeric form.

The invention will now be described in greater detail by way of the following examples, wherein the temperatures are indicated in degrees centigrade and the abbreviations have the usual meaning in the art.

EXAMPLE 1

Preparation of
(1RS,5RS)-5-methyl-exo-tricyclo[6.2.1.0$^{2,7}$]undecan-4-one a) 4-Methyl-exo-tricyclo[6.2.1.0$^{2,7}$]undecan-4ene This compound was prepared in a manner identical to that described in example 8 of U.S. Pat. No. 3,968,070, by reacting norbornene with isoprene at a temperature of about 150°. After the usual treatment, the desired product was obtained with 99% purity. The analytical characters of this product were the following:
NMR($^1$H, 360 MHz): 5.48(m, 1H); 2.20–1.95(m, 2H); 1.90(broad s, 2H); 1.69(s, 3H); 1.65–1.41(m, 7H); 1.18(dd, J=7 Hz, 2.5 Hz, 2H); 1.0(d, J=11 Hz, 1H) δppm
NMR($^{13}$C, 90 MHz): 136.8(s); 121.5(d); 43.4(2d); 43.3(d); 43.2(d); 33.4(2t); 29.9(t); 29.8(t); 28.4(t); 23.3(q) δppm
MS: 162(M$^+$, 57), 147(23), 134(38), 133(36), 119(25), 106 (24), 105(32), 95(30), 94(63), 93(63), 92(41), 91(70), 79(100), 78(20), 77(49), 67(41), 66(82), 65(26), 53(19), 41 (31), 39(27)

b) (1RS,4RS)-4,5-Epoxy-4-methyl-exo-tricyclo[6.2.10$^{2,7}$]undecane

The compound prepared according to a) was reacted with 40% peracetic acid, in methylene chloride, in identical manner to that described in example 8 of U.S. Pat. No. 3,968,070. After similar treatment to that there-described, there was obtained a product containing around 83% by weight of 1RS,4RS)-4,5-epoxy-4-methyl-exo-tricyclo [6.2.1.0$^{2,7}$]undecane, together with about 17% by weight of (1RS,4SR)-4,5-epoxy-4-methyl-exo-tricyclo[6.2.1.0$^{2,7}$]undecane.

The analytical characters of the two isomers were as follows:
A. (1RS,4SR)-4,5-epoxy-4-methyl-exo-tricyclo[6.2.1.0$^{2,7}$] undecane (17%):
NMR($^{13}$C, 90 MHz) visible peaks: 57.4(d); 56.2(s); 41.9(d); 41.7(d); 40.7(d); 40.6(d); 34.7(t); 32.0(t); 29.6(20; 21.9(q) δppm
MS: 178(M$^+$, 24), 163(12), 150(40), 149(30), 136(39), 134 (17), 121(15), 119(15), 111(23), 109(22), 108(22), 107(30), 106(22), 95 (30), 94(23), 93(52), 92(43), 91(42), 82(25), 81(66), 80(38), 79(76), 77(37), 67(100), 66(47), 55(30), 53(22), 43(52), 41(48), 39(28)
B. (1RS,4RS )-4,5-epoxy-4-methyl-exo-tricyclo[6.2.1.0$^{2,7}$] undecane (83%):
NMR($^1$H, 360 MHz): 2.90(d, J=3.6 Hz, 1H); 2.15(m, 1H); 1.95(dd, J=14 Hz, 7 Hz, 1H); 1.82(broad s, 2H); 1.71–1.32(m, 7H); 1.26(s, 3H); 1.21–1.12(m, 2H); 1.05–0.96(m, 1H) δppm
NMR($^{13}$C, 90 MHz): 57.8(d); 55.6(s); 42.1 (d); 42.0(d); 39.8(d); 38.0(d); 33.2(t); 32.8(t); 29.4(0; 29.3(t); 28.0(t); 22.5(q) δppm
MS: 178(M$^+$, 23), 163(15), 150(32), 149(77), 136(29), 134 (15), 121(17), 119(18), 111(26), 109(21), 107(30), 95(26), 94(20), 93(56), 92(48), 91(50), 82(19), 81(81), 80(34), 79(69), 77(36), 67(100), 66(38), 65(21), 55(28), 43(51), 41(58), 39(27)

This mixture of epoxides possesses useful odor properties, developing an ambery note reminiscent of that which is characteristic of ambrinol, aromatic and fruity, of the melon type.

c) (1RS,5SR)-5-Methyl-exo-tricyclo[6.2.1.0$^{2,7}$]undecan-4-one

The mixture of epoxides described under b) was isomerised by means of boron trifluoride etherate, followed by sodium bicarbonate, as is described in the above-mentioned U.S. patent.

After the usual treatment, the product obtained was a mixture containing about 80% by weight of (1RS,5SR)-5-methyl-exo-tricyclo[6.2.1.0$^{2,7}$]undecan-4-one and about 20% by weight of its (1RS,5RS) isomer.

The analytical characters of this mixture coincided with those indicated in U.S. Pat. No. 3,968,070.

d) A 3 1 4-neck flask, equipped with a magnetic stirrer, a 15 cm Vigreux column, and a thermometer, was charged with 1400 g of the mixture obtained according to c) in 1000 g of toluene. There was added thereto, all at once, 13.0 g (0.072 mole) of 30% sodium methylate in methanol. The reaction mixture turned orange and the reaction was slightly exothermic. The mixture was kept under stirring at room temperature during 50 minutes.

Glacial acetic add was then added thereto (4.3 g; 0,072 mole) and the mixture turned yellow. The solvent was first distilled under atmospheric pressure, then under partial vacuum to provide a raw product (1405 g) which, once purified by distillation, gave a 96% pure mixture containing about 78% of (1RS,5RS)-5-methyl-exo-tricyclo[6.2.1.0$^{2,7}$] undecan-4-one and 2.2% of its (1RS,5SR) isomer. This mixture possessed the odor properties described earlier on in the specification, i.e. an aromatic, thujonic, herbaceous type odor, reminiscent of myrtle and cedarleaf.

The two stereoisomers contained in the mixture were separated by either preparative chromatography (silica column: 1 kg; solvent cyclohexane/tert-butyl methyl ether 95/5), or by fractional distillation on a multiple plate column of the Fischer Spaltrohr® type, 1 m long, under vacuum. The following compounds were thus obtained:
A. (1RS,5RS)-5-methyl-exo-tricyclo[6.2.1.0$^{2,7}$]undecan-4-one:
Purity: 94%
B.p. 96°/3×10$^2$ Pa
NMR($^1$H, 360 MHz): 2.32–1.92(m, 5H); 1.87–1.70(m, 3H); 1.67–1.49(m, 3H); 1.40–1.10(m, 4H); 1.08(d, J=7 Hz, 3H) δppm
NMR($^{13}$C, 90 MHz): 216.1(s); 43.0(d); 42.6(2d); 41.8(d); 41.5(t); 39.9(d); 33.8(t); 32.4(0; 29.6(0; 28.8(t); 16.0(q) δppm
MS: 178(M$^+$, 37), 150(52), 136(83), 135(17), 134(29), 121 (18), 119(14), 109(33), 108(30), 107(36), 106(35), 95(42), 94(31), 93 (54), 91(36), 82(48), 81(73), 80(40), 79(79), 77(34), 67(100), 66(41), 55(30), 53(24), 41(38)
B. (1RS,5SR)-5-methyl-exo-tricyclo[6.2.1.0$^{2,7}$]undecan-4-one:
Purity: 95%
NMR($^1$H, 360 MHz): 2.42–2.13(m, 3H); 1.98(broad s, 2H); 1.88–1.50(m, 7H); 1.40–1.02(m, 3H); 1.12(d, J=7 Hz, 3H) δppm
NMR($^{13}$C, 90 MHz): 216.7(s); 42.7(d); 42.3(t); 41.7(d); 41.0(d); 40.3(d); 37.6(d); 32.4(t); 31.8(t); 29.7(t); 28.9(t); 16.1(q) δppm
MS: 178(M$^+$, 36), 150(55), 136(62), 134(20), 121(18), 109 (26), 108(26), 107(28), 106(27), 95(26), 94(20), 93(38), 91(27), 82(32), 81(56), 80(34), 79(75), 73(34), 68(22), 67(100), 66(41), 65(21), 55(32), 53(25), 41(56), 39(31)

EXAMPLE 2

Perfuming Composition

A base perfuming composition was prepared with the following ingredients:

| Ingredients | Parts by weight |
| --- | --- |
| Exolide ®[1] | 5 |
| Methyl geranate | 3 |
| Synth. geranium oil | 35 |
| Lavandin essential oil | 30 |
| 10% *Oakmoss absolute | 15 |
| Amyl salicylate | 7 |
| Total | 95 |

*in dipropyleneglycol (DIPG)
[1] pentadecanolide; origin: Firmenich SA, Geneva, Switzerland With this base composition of the fougere type, there was prepared a composition A by addition of 5 parts by weight of the prior art product rich in (1RS,5SR)-5-methyl-exo-tricyclo[6.2.1.0$^{2,7}$]undecan-4-one, described in example 1c), and a novel composition B obtained by adding to the base 5 parts by weight of the mixture according to the invention, rich in (1RS,5RS)- 5-methyl-exo-tricyclo[6.2.1.0$^{2,7}$]undecan-4-one and described in example 1 d).

Compositions A and B were then evaluated on a blind test by a panel of expert perfumers. The latter unanimously preferred composition B for its far more natural odor, in particular as regards the aromatic note, and for its stronger herbaceous connotation.

Furthermore, the perfumers also preferred another novel composition prepared by adding to the base composition 5 parts by weight of 94% pure (1RS,5RS)-5-methyl-exo-tricyclo[6.2.1.0$^{2,7}$]undecan-4-one. In their opinion, the addition of this compound enhanced even more the fragrance effect of the aromatic, thujonic, herbaceous type already observed with the mixture which contained a predominant amount of said compound.

EXAMPLE 3

Perfuming Composition for a Shampoo

A base perfuming composition intended for perfuming a shampoo was prepared by admixing the following ingredients:

| Ingredients | Parts by weight |
| --- | --- |
| Styrallyl acetate | 25 |
| 50% *Dodecanal | 10 |
| Hexylcinnamic aldehyde | 20 |
| 10% *Methyl-nonyl-acetaldehyde | 30 |
| 10% *Allyl amyl glycolate | 20 |
| 10% *4-Nonalide[1] | 5 |
| 1-Carvone | 70 |
| Citronellol | 140 |
| Allyl cyclohexylpropanoate | 5 |
| Dihydromyrcenol[2] | 110 |
| Hedione ®[3] | 60 |
| Geranyl nitrile | 5 |
| Lilial ®[4] | 15 |
| Linalol | 120 |
| Menthol | 30 |
| Nerol | 35 |
| Petitgrain essential oil | 60 |
| Phenylethyl alcohol | 100 |
| Sweet orange essential oil | 40 |
| Hexyl salicylate | 10 |
| (Z)-3-Hexenyl salicylate | 5 |
| Terpineol | 15 |
| Tonalid ®[5] | 25 |
| Vert de lilas ®[6] | 15 |
| Zestover ®[7] | 10 |
| Total | 980 |

*in dipropyleneglycol (DIPG)
[1] origin: Firmenich SA, Geneva, Switzerland
[2] 2,6-dimethyl-7-octen-2-ol; origin: International Flavors & Fragrances, USA
[3] methyl dihydrojasmonate; origin: Firmenich SA, Geneva, Switzerland
[4] 3-(4-tert-butyl-1-phenyl)-2-methylpropanal; origin: Givaudan-Roure, Vernier, Switzerland
[5] 7-acetyl-1,1,3,4,4,6-tetramethyltetraline; origin: PFW, Holland
[6] (2,2-dimethoxyethyl)-benzene; origin: Givaudan-Roure, Vernier, Switzerland
[7] 2,4-dimethyl-3-cyclohexene-1-carbaldehyde; origin: Firmenich SA, Geneva, Switzerland To this base composition of the aromatic, floral, green, citrus type, there were added 20 parts by weight of the mixture of ketones according to the invention, prepared as described in example 1 d), to obtain a novel composition A, and the same amount of the prior art mixture containing essentially (1RS,5SR)-5-methyl-exo-tricyclo[6.2.1.0$^{2,7}$]undecan-4-one to obtain a composition B.

When compositions A and B were evaluated by a panel of ten perfumers, on a blind test, it appeared that the odor of composition A had a lot more lift and volume, and a more natural character, than that of composition B.

According to the perfumers, the addition of the mixture of the invention particularly exhalted the odor character imparted by 1-carvone, whereas the addition of the prior art mixture, because of its camphoraceous note, blurred and toned down its freshness.

EXAMPLE 4

Perfuming of Textiles

To a non-perfumed fabric softener base of commercial origin there was added 0.1% by weight of (1RS,5RS)-5-methyl-exo-tricyclo[6.2-1.0$^{2,7}$]undecan- 4-one, or of a mixture according to the invention containing about 80% by weight of this compound, to obtain a perfumed softener, which was then used to treat a standard batch of fabrics during a normal washing cycle in a washing machine.

The fabrics were then evaluated by a panel of four expert perfumers, both just out of the machine and after drying. According to their opinion, the textiles developed a strong and very pleasant odor with an aromatic, thujonic and herbaceous character, which reminded them of the odor of myrtle and cedarleaf.

This batch of fabrics was also compared, on a blind test, with another standard batch of textiles which had been treated in a similar manner, but in the presence of a fabric softener perfumed by means of the known mixture containing essentially the (1RS,5SR) isomer of the above-mentioned ketone. In the perfumers' opinion, the latter batch of textiles developed a far less fresh odor, more camphoraceous than that of the first batch, which they preferred. They observed, moreover, that the fragrance of the first batch was not only distinct from that of the second, but also far more powerful, and that it remained on the fabrics far longer than that of the second batch.

What we claim is:

1. A composition consisting of a mixture which contains more than 50% by weight of (1RS,5RS)-5-methyl-exo-tricyclo[6.2.1.0$^{2,7}$]undecan-4-one, together with a lesser amount of (1RS,5SR)-5-methyl-exo-tricyclo[6.2.1.0$^{2,7}$]undecan-4-one.

2. A composition according to claim 1, containing 75% by weight or more of (1RS,5RS)-5-methyl-exo-tricyclo[6.2.1.0$^{2,7}$]undecan-4-one and not more than 25% by weight of (1RS,5SR)-5-methyl-exo-tricyclo[6.2.1.0$^{2,7}$]undecan-4-one.

3. The composition of claim 2, which consists of about 78% by weight of (1RS,5RS)-5-methyl-exo-tricyclo[6.2.1.0$^{2,7}$]undecan-4-one and about 22% by weight of (1RS,5SR)-5-methyl-exo-tricyclo[6.2.1.0$^{2,7}$]undecan-4-one.

4. (1RS,5RS)-5-Methyl-exo-tricyclo[6.2.1.0$^{2,7}$]undecan-4-one having a purity above 90%.

5. A method to impart, improve, enhance or modify the odor properties of a perfuming composition or of a perfumed article, which consists in adding to said composition or article a fragrance effective amount of the composition of claim 1.

6. A method to impart, improve, enhance or modify the odor properties of a perfuming composition or of a perfumed article, which consists in adding to said composition or article a fragrance effective amount of essentially pure (1RS,5RS)-5-methyl-exo-tricyclo[6.2.1.0$^{2,7}$]undecan-4-one.

7. A perfuming composition or a perfumed article containing as perfuming ingredient the composition of claim 1.

8. A perfuming composition or a perfumed article containing as perfuming ingredient essentially pure (1RS,5RS)-5-methyl-exo-tricyclo[6.2.1.0$^{2,7}$]undecan-4-one.

9. A perfumed article according to claim 7, as a perfume or a cologne, a soap, a bath or shower gel, a shampoo or a hair conditioner, a cosmetic preparation, a body deodorant, an air freshener, a detergent or a fabric softener, or a household product.

10. A process for the preparation of a composition according to claim 1, which comprises treating a mixture of (1RS,5RS)-5-methyl-exo-tricyclo[6.2.1.0$^{2,7}$]undecan-4-one and (1RS,5SR)-5-methyl-exo-tricyclo[6.2.1.0$^{2,7}$]undecan-4-one, wherein the latter is present in a preponderant amount, with a strong organic or inorganic base at an appropriate temperature and for an amount of time sufficient to obtain the desired composition.

11. The process of claim 10, wherein the strong base is an alkali metal alkoxide or hydroxide.

12. The process of claim 10, wherein a mixture containing about 80% by weight of (1RS,5SR)-5-methyl-exo-tricyclo[6.2.1.0$^{2,7}$]undecan-4-one and about 20% by weight of (1RS,5RS)-5-methyl-exo-tricyclo[6.2.1.0$^{2,7}$]undecan-4-one is treated with sodium methylate, to thereby provide a composition containing about 78% by weight (1RS,5RS)-5-methyl-exo-tricyclo[6.2.1.0$^{2,7}$]undecan-4-one and about 22% by weight of (1RS,5SR)-5-methyl-exo-tricyclo[6.2.1.0$^{2,7}$]undecan-4-one.

13. The process of claim 10, wherein the composition is further subjected to preparative chromatography or to fractional distillation and essentially pure (1RS,5RS)-5-methyl-exo-tricyclo[6.2.1.0$^{2,7}$]undecan-4-one is thereby obtained.

* * * * *